United States Patent [19]
Zask et al.

[11] Patent Number: 5,128,328
[45] Date of Patent: Jul. 7, 1992

[54] HETEROCYCLIC BISPHOSPHONIC ACID DERIVATIVES

[75] Inventors: Arie Zask, New York, N.Y.; Richard D. Coghlan, Spotswood, N.J.

[73] Assignee: American Home Products Corporation, New York, N.Y.

[21] Appl. No.: 783,053

[22] Filed: Oct. 25, 1991

[51] Int. Cl.$^5$ .............. A61K 31/675; C07F 9/06; C07F 9/28
[52] U.S. Cl. .............. 514/89; 514/92; 546/22; 548/111
[58] Field of Search .............. 548/111; 546/22; 514/89, 92

[56]  References Cited
U.S. PATENT DOCUMENTS
4,503,049  3/1985  Biere et al. .............. 514/80

Primary Examiner—Mary C. Lee
Assistant Examiner—Joseph K. McKane
Attorney, Agent, or Firm—Richard K. Jackson

[57] ABSTRACT

The compound of the formula:

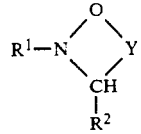

in which

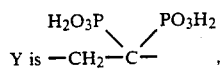

positioned so that the gem-diphosphonic acid carbon atom is in the 4- or 5-position; $R^1$ is alkyl or arylalkyl; $R^2$ is hydrogen, 2- or 3-pyridinyl or 3-,5- or 6-alkylpyridin-2-yl; or a pharmaceutically acceptable salt thereof, with the proviso that when the gem-bisphosphonic acid substituted carbon atom is in 4-position, $R^1$ is other than alkyl, used in the treatment of disease states involving calcium metabolism.

16 Claims, No Drawings

HETEROCYCLIC BISPHOSPHONIC ACID DERIVATIVES

BACKGROUND OF THE INVENTION

A number of heterocyclic bisphosphonic acid derivatives useful in treating disorders of calcium metabolism such as Morbus Paget, osteoporosis, Morbus Bechterew, arthritis, etc. have appeared in the literature. Exemplary of these compounds are the pyrrolidone-5,5-diphosphonic acid derivatives disclosed in Belgian Patent 819,187, granted Feb. 26, 1975; the piperidinone diphosphonic acid derivatives of German Offenlegungsschrift 25 53 963, published Jun. 6, 1977 and the oxazine bisphosphonic acid disclosed in German Offenlegungsschrift 37 19513, published Dec. 22, 1988.

DESCRIPTION OF THE INVENTION

In accordance with this invention, there is provided a group of heterocyclic bisphosphonic acid derivatives of the formula:

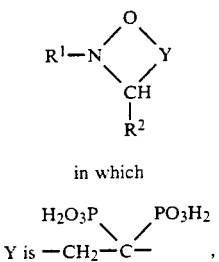

in which $$Y \text{ is } -CH_2-\underset{\underset{PO_3H_2}{|}}{\overset{\overset{H_2O_3P}{|}}{C}}-,$$

positioned so that the gem-diphosphonic acid carbon atom is in the 4- or 5- position;

$R^1$ is alkyl of 1 to 6 carbon atoms or arylalkyl of 7 to 12 carbon atoms;

$R^2$ is hydrogen, 2- or 3-pyridinyl or 3-,5- or 6-alkylpyridin-2-yl in which the alkyl substituent has 1 to 6 carbon atoms;

or a pharmaceutically acceptable salt thereof, with the proviso that when the gem-bisphosphonic acid substituted carbon atom is in 4-position, $R^1$ is other than alkyl.

The pharmaceutically acceptable salts are derived from acids or bases. The bases employed in the production of these salts provide a cation from the alkali-metal or alkaline earth metal groups or ammonium hydroxide. Acceptable salts may also be derived from known inorganic or organic acids such as hydrochloric, hydrobromic, sulfuric, nitric, phosphoric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, para-amino benzoic, para-hydroxybenzoic, salicylic, sulfanilic acids, and the like.

The preferred compounds are those in which the free phosphonic acids appear in the 5-position, $R^1$ is methyl and $R^2$ is hydrogen, 2- or 3-pyridinyl or 3- or 5-methylpyridin-2-yl.

The most preferred compounds are those in which the free phosphonic acid groups are in the 5-position, $R^1$ is methyl and $R^2$ is 2-pyridinyl or 3-methylpyridin-2-yl.

The compounds of this invention are prepared by reaction of an appropriately substituted nitrone $R^2CH=N(O)R^1$ with a tetraalkyl ethenylidinebisphosphonate $H_2C=C(PO_3R_2)_2$ followed by conversion to the free acids with trimethylsilyl bromide in carbon tetrachloride followed by alcohol hydrolysis of the silyl ester or direct hydrolysis with aqueous hydrochloric acid. The nitrones and their aldehyde precursors are commercially available or prepared by literature methods. The 1,3-dipolar addition of nitrones to olefinic unsaturation is known.

The compounds of this invention contain a chiral center when $R^2$ is other than hydrogen. Hence, the product is obtained as a racemic mixture which may be resolved into the enantiomers conventionally. Reference to the compound name throughout this application is intended to embrace the racemic mixture or either optical isomer.

The compounds of this invention are inhibitors of bone resorption useful in the treatment of osteoporosis and disease states in which calcium metabolism is to be modified such as in Pagets' disease, hypercalcemia of malignancy, and the like. The ability of these bisphosphonates to inhibit bone resorption was established following the standard test procedures disclosed in Raisz, J. Clin. Invest. 44, 103 (1965) and Stern et al., Calcif. Tissue Int. 35, 172 (1983).

In accordance with these procedures, the percentage of $^{45}Ca$ released from fetal rat limb bones into an incubation medium containing parathyroid hormone (PTH) is determined in the presence and absence of a test compound. The results are expressed as the percent reduction of $^{45}Ca$ release of the experimental group versus the vehicle control group or as the inhibitory concentration of compound which reduces by half the $^{45}Ca$ release stimulated by PTH ($IC_{50}$). The results of this study are reported in the following Table under PTH.

The in vivo activity of the compounds of this invention was established by determining the ability of the test compound to prevent reduction in bone mass from denervated rat limbs (osteopenia). In this procedure, female, Sprague Dawley CD ® rats, 225 to 250 g, are individually weighed, anesthetized and a portion of the sciatic nerve adjacent to caudo-femoralis and adductor brevis muscles is removed from the left hind leg. After a post-surgery recovery period, the test compound is administered either orally or parenterally five days a week for four weeks. The animals are humanely euthenized and the femora and tibiae are removed from both limbs. The body weight, femur mass (dried or ashed) and trabecular (cancellous) bone mineral area are determined. The results are reported in the following Table as the percentage reduction in femur mass loss of the drug treated group compared with the control group.

TABLE

| Example | In Vivo (mg/kg) | PTH |
|---|---|---|
| 1 | 10, i.p. 37% ($p < 0.05$) | 67% at 1 ug/mL |
| 2 | | $IC_{50}$ = 5 ug/mL |
| 3 | 20, p.o. 48% ($p < 0.05$) | 46% at 0.1 ug/mL |
| 4 | | 53% at 10 ug/mL |
| 5 | 10, p.o. 31% ($p < 0.05$) | 61% at 1 ug/mL |
| 6 | | $IC_{50}$ = 0.712 ug/mL |
| 7 | | 44% at 5 ug/mL |
| 8 | 10, p.o. 17% ($p < 0.05$) | 46% at 5 ug/mL |
| 9 | | 54% at 1 ug/mL |

Based upon the data obtained in these standard experimental test procedures, the compounds of this invention are useful in regulating bone calcium metabolism by preventing resorption. As such, the compounds are useful in treating patients suffering from osteoporosis, Pagets' disease, hypercalcemia of malignancy, and the like, by oral or parenteral administration of a bone mass stabilizing amount of a pharmaceutical composition containing a compound of this invention alone or in conjunction with known regulators of calcium metabolism such as calcitonin (salmon, porcine, human, etc.) or sodium fluoride, and a pharmaceutically acceptable carrier.

The dosage level for administration will vary from patient to patient based upon age, weight, size, degree of bone mass loss, and response to chronic compound administration, as well as the route of administration. The dosage must be subjectively determined by the attending physician. Based upon the experimental test data, the dosage regimen should begin at about 5 mg/kg/day and be varied subsequently to from about 1 to about 100 mg/kg/day depending upon the concentration of calcium in blood serum and/or absence of continued bone mass loss and/or increase in bone mass.

The following examples illustrate without limitation the preparation of representative compounds of this invention.

EXAMPLE 1

(2-Methyl-5-isoxazolidenylidene)bisphosphonic acid

To a solution of ethenylidenebisphosphonate (4.69 g, 16.5 mmol), sodium acetate (1.23 g, 15.0 mmol) and 37% aqueous formaldehyde (1.50 mL, 19.9 mmol) in dioxane (25 mL) at 25° C. was added, dropwise over 3 hours, a solution of N-methylhydroxylamine hydrochloride (1.23 g, 15.0 mmol) in 10:1 dioxane:water (5 mL). The reaction mixture was stirred 18 hours then concentrated in vacuo. The resulting oily solid was treated with a minimum of water to effect solution, then saturated with solid $NaHCO_3$. The resulting paste was washed repeatedly with ethyl acetate. The combined organic washings were dried over $K_2CO_3$, then concentrated in vacuo to give tetraethyl (2-methyl-5-isoxazolidenylidene)bisphosphonate as a pale yellow oil (5.43 g).

MS (+FAB) m/e: 360 (M+H$^+$). $^1$H NMR (acetone-d$_6$, 200 MHz): δ 1.30 (t, J=8 Hz, 12H, —CH$_2$CH$_3$), 2.6–3.0 (m, 3H, —NCHHCH$_2$—), 2.71 (s, 3H, NCH$_3$), 3.3–3.5 (m, 1H, —NCHH—), 4.0–4.4 (m, 8H, —OCH$_2$).

The product of the preceding paragraph was dissolved in 6N aqueous HCl and the solution was heated at 100° C. for a period of 24 hours. The water was evaporated and the residue was triturated with ethanol to afford a white powder, 1.59 grams (40% yield) of the title compound as the partial hydrochloride salt, m.p. 144° C. (dec).

MS (−FAB) m/e: 246 (M−H$^+$). $^1$H NMR (D$_2$O, 400 MHz): δ 2.73–3.05 (m, 2H, —NCH$_2$CH$_2$—), 3.18 (s, 3H, —CH$_3$), 3.44–3.57 (m, 1H, —NCHH—), 3.98–4.08 (m, 1H, —NCHH—). $^{13}$C NMR (D$_2$O, 100 MHz): δ 33.2 (strong, —CH$_3$), 43.8 (strong, —NCH$_2$CH$_2$—), 57.0 (medium, —NCH$_2$—), 86.3 (t, J=142 Hz, weak, —PCP—).

Elemental analysis for $C_4H_{11}NO_7P_2 \cdot 0.95$ HCl: Calc'd: C, 17.05; H, 4.28; N, 4.97. Found: C, 17.43; H, 4.56; N, 4.58.

EXAMPLE 2

[2-(Phenylmethyl)-5-isoxazolidenylidene]bisphosphonic acid

To a stirred solution of ethenylidenebisphosphonate (6.91 g, 23.0 mmol) and 30% aqueous formaldehyde (2.46 g, 30.3 mmol) in dioxane (25 mL) was added solid sodium acetate (2.13 g, 25.7 mmol). A solution of N-benzylhydroxylamine hydrochloride (4.08 g, 25.3 mmol) in water (ca. 10 mL) was then added dropwise via syringe pump over 1.75 hours at 25° C. After the addition was complete, the reaction mixture was concentrated in vacuo. The resulting residue was taken up in a minimum amount of water, neutralized and saturated with solid sodium bicarbonate, and extracted with ethyl acetate (3×). The combined organic extracts were dried ($K_2CO_3$) and concentrated in vacuo to give 9.81 g (98% yield) of oil. The oil was chromatographed on 300 g silica gel ($CH_2Cl_2$:MeOH/NH$_3$, 95:5) to give 7.03 g (70% yield) of tetraethyl [2-(phenylmethyl)-5-isoxazolidenylidene] bisphosphonate as a colorless oil.

IR (neat) 1440 (m, doublet), 1242 (s, P=O), 1020 (s), 962 (s), 730 (m), 690 (m) cm$^{-1}$. MS (FAB) m/e (rel. intensity) 436 (M+H$^+$, 57), 298 (M−PO$_3$Et$_2$, 33), 91 (PhCH$_2^+$, 100). $^1$H NMR (D$_2$O, 200 MHz) δ 1.20 (m, 12H, CH$_2$CH$_3$), 2.55–3.15 (overlapping m, 3H, NCH$_2$CH$_2$, NCHHCH$_2$), 3.35 (broad, 1H, NCHHCH$_2$), 3.85–4.25 and 4.01 (overlapping m and s, 10H, CH$_2$CH$_3$ and NCH$_2$Ar), 7.30 (m, 5H, ArH).

The product of the preceding paragraph was dissolved in carbon tetrachloride and ten mole equivalents of trimethylsilyl bromide (TMSBr) was added. The solution mole was left at room temperature for about seventy hours at which time the carbon tetrachloride was removed by distillation and the residue was triturated with aqueous ethanol to give 2.57 grams (77% yield) of the title compound as a white powder, m.p. 149° C. (dec.).

IR (KBr) 3420 (m, broad), 1462 (m), 1198 (s), 1070 (s, broad), 997 (s), 752 (m) cm$^{-1}$. MS (negative FAB) m/e (rel. intensity) 322 (M−H$^+$, 100). $^1$H NMR (D$_2$O, 400 MHz) δ 2.66–2.96 (overlapping m, 2H, NCH$_2$CHH), 3.64 (dd, J=8 Hz, 20 Hz, 1H, NCHHCH$_2$), 3.82 (m, 1H, NCHHCH$_2$), 4.54 (t, J=13 Hz, 1H, NCH$_2$), 7.26–7.42 (m, 5H, ArH).

Elemental analysis for $C_{10}H_{15}NO_7P_2 \cdot 0.1$ $H_2O$: Calc'd: C, 36.96; H, 4.71; N, 4.31. Found: C, 36.71; H, 4.45; N, 4.43.

EXAMPLE 3

[2-Methyl-3-(2-pyridinyl)-5-isoxazolidenylidene]bisphosphonic acid

A mixture of ethenylidenebisphosphonate (13.73 g, 45.8 mmol) and N-(2-pyridinylmethylene)methanamine N-oxide (3.11 g, 22.9 mmol) was heated at 60° C. for 18 hours. The resulting oil was chromatographed on 250 g silica gel (ethyl acetate:MeOH/NH$_3$, 20:1) to give 9.56 g (96% yield) of tetraethyl [2-methyl-3-(2-pyridinyl)-5-isoxazolidenylidene] bisphosphonate as an oil.

MS (FAB) m/e (rel. intensity) 437 (M+H$^+$, 34). $^1$H NMR (D$_2$O, 200 MHz) δ 1.30 (m, 12H, POCH$_2$CH$_3$), 267 (s, 3H, NCH$_3$), 3.05 (m, 2H, CHCH$_2$), 3.94 (broad t, J=8.5 Hz, 1H, CHCH$_2$), 4.24 (m, 8H, POCH$_2$CH$_3$), 7.35 (dd, J=5 Hz, 8 Hz, 1H, pyr-H), 7.46 (d, J=8 Hz, 1H, pyr-H), 7.82 (t, J=8 Hz, 1H, pyr-H), 8.40 (d, J=5 Hz, 1H, pyr-H).

Procedure as described in Example 2 using TMSBr. Reaction time: 71 hours. Trituration with methanol gave 1.98 g (38% yield) of [2-methyl-3-(2-pyridinyl)-5-isoxazolidenylidene] bisphosphonic acid as a green powder, m.p. 115° C. (dec.).

IR (KBr) 3400 (m, broad), 2750 (m, broad), 1625 (m), 1465 (m), 920 (m, broad), 768 (m) cm$^{-1}$. MS (negative FAB) m/e (rel. intensity) 323 (M−H+, 100). $^1$H NMR (D$_2$O, 400 MHz) δ 2.72 (s, 3H, NCH$_3$), 2.92 (m, 1H, CHCHH), 3.34 (m, 1H, CHCHH), 4.47 (broad t, 1H, CHCH$_2$), 7.92 (t, J=6 Hz, 1H, pyr-H), 8.02 (d, J=8 Hz, 1H, pyr-H), 8.49 (t, J=8 Hz, 1H, pyr-H), 8.68 (d, J=6 Hz, 1H, pyr-H). $^{13}$C NMR (D$_2$O, 100 MHz) δ 42.3, 43.1, 68.5, 80.9 (t, J=144 Hz), 126.5, 126.9, 142.0, 146.8, 151.6.

EXAMPLE 4

[2-Methyl-3-(3-pyridinyl)-5-isoxazolidenylidene]bisphosphonic acid

A mixture of ethenylidenebisphosphonate (8.07 g, 26.9 mmol) and N-(3-pyridinylmethylene)methanamine N-oxide (1.83 g, 13.5 mmol) was heated at 62° C. for 17 hours. The resulting oil was chromatographed on 300 g silica gel (ethyl acetate:MeOH/NH$_3$, 20:1) to give 2.98 g (51% yield) of tetraethyl [2-methyl-3-(3-pyridinyl)-5-isoxazolidenylidene] bisphosphonate as an oil.

$^1$H NMR (D$_2$O, 200 MHz) δ 1.30 (t, J=7 Hz, 12H, POCH$_2$CH$_3$), 2.54 (s, 3H, NCH$_3$), 2.95 (m, 2H, CHCH$_2$), 3.84 (broad t, 1H, CHCH$_2$), 4.24 (p, J=7 Hz, 8H, POCH$_2$CH$_3$), 7.38 (m, 1H, pyr-H), 7.79 (d, J=9 Hz, 1H, pyr-H), 8.42 (broad s, 2H, pyr-H).

Follow the procedure of Example 2 using TMSBr. Reaction time: 5 days. Trituration with methanol gave 1.40 g (53% yield) of [2-methyl-3-(3-pyridinyl)-5-isoxazolidenylidene] bisphosphonic acid hydrobromide as a white powder, m.p. 151° C. (dec.).

IR (KBr) 3400 (m, broad), 3070 (m), 2780 (m, broad), 1640 (m), 1563 (m), 1475 (m), 920 (s), 688 (m) cm$^{-1}$. MS (negative FAB) m/e (rel. intensity) 323 (M−H+, 100). $^1$H NMR (D$_2$O, 400 MHz) δ 2.75 (s, 3H, NCH$_3$), 2.95 (m, 1H, CHCHH), 3.25 (m, 1H, CHCHH), 4.41 (broad, 1H, CHCH$_2$), 8.08 (dd, J=6 Hz, 8 Hz, 1H, pyr-H), 8.72 (d, J=8 Hz, 1H, pyr-H), 8.77 (d, J=6 Hz, 1H, pyr-H), 8.93 (s, 1H, pyr-H). $^{13}$C NMR (D$_2$O, 100 MHz) δ 42.3, 43.1, 69.2, 81.2 (t, J=148 Hz), 127.6, 135.6, 141.2, 141.5, 146.7.

Elemental analysis for C$_9$H$_{14}$N$_2$O$_7$P$_2$·1.0 HBr·1.8 H$_2$O: Calc'd: C, 24.71; H, 4.29; N, 6.40. Found: C, 24.75; H, 4.68; N, 6.78.

EXAMPLE 5

[2-Methyl-3-(3-methyl-2-pyridinyl)-5-isoxazolidenylidene]bisphosphonic acid

A mixture of ethenylidenebisphosphonate (6.67 g, 22.2 mmol) and N-[(3-methyl-2-pyridinyl)methylene]methanamine N-oxide (4.01 g, 26.7 mmol) was heated at 40° C. for 2 hours. The resulting oil was chromatographed on 500 g silica gel (ethyl acetate:Et$_3$N, 100:1) to give 8.10 g (81% yield) of tetraethyl [2-methyl-3-(3-methyl-2-pyridinyl)-5-isoxazolidenylidene] bisphosphonate as a clear, colorless, viscous liquid.

$^1$H NMR (CDCl$_3$, 400 MHz) δ 1.35 (m, 12H, CH$_2$CH$_3$), 2.44 (s, 3H, pyr-CH$_3$), 2.70 (broad s, 3H, NCH$_3$), 2.95 (broad s, 1H, CHCHH), 3.40 (broad s, 1H, CHCHH), 4.15 (t, J=7 Hz, 1H, CHCH$_2$), 4.30 (m, 8H, CH$_2$CH$_3$), 7.10 (dd, J=5 Hz, 8 Hz, 1H, pyr-H), 7.44 (d, J=8 Hz, 1H, pyr-H), 8.45 (d, J=5 Hz, 1H, pyr-H).

Follow the procedure described in Example 2 using TMSBr. Reaction time: 90 hours. Trituration with methanol gave 2.3 g (72% yield) of [2-methyl-3-(3-methyl-2-pyridinyl)-5-isoxazolidenylidene] bisphosphonic acid as a tan powder, m.p. 139° C. (dec.).

IR (KBr) 3385 (m), 2850 (m, broad), 1605 (m), 1517 (m), 1455 (m), 1200 (m), 940 (s, broad), 790 (m) cm$^{-1}$. MS (negative FAB) m/e (rel. intensity) 337 (M-H, 100).

$^1$H NMR (D$_2$O, 400 MHz) δ 2.49 (s, 3H, pyr-CH$_3$), 2.65–2.85 and 2.73 (overlapping m and s, 4H, CHCHH and NCH$_3$), 3.35 (m, 1H, CHCHH), 4.58 (t, J=8 Hz, 1H, CHCH$_2$), 7.78 (dd, J=6 Hz, 8 Hz, 1H, pyr-H), 8.30 (d, J=8 Hz, 1H, pyr-H), 8.49 (d, J=6 Hz, 1H, pyr-H).

EXAMPLE 6

[2-Methyl-3-(5-methyl-2-pyridinyl)-5-isoxazolidenylidene]bisphosphonic acid

A mixture of ethenylidenebisphosphonate (10.2 g, 34 mmol) and N-[(5-methyl-2-pyridinyl)methylene]methanamine N-oxide (2.6 g, 17 mmol) was heated at 55° C. for 3.25 hours. The resulting oil was cooled, dissolved in chloroform (60 mL) and extracted with 0.25N aqueous HCl (3×60 mL). The pale green aqueous extracts were combined then neutralized and saturated with solid sodium bicarbonate, whereupon the solution turned brown. The aqueous phase was extracted with ethyl acetate (4×180 mL). The combined organic extracts were dried (K$_2$CO$_3$) and concentrated in vacuo to give 5.4 g (70% yield) of light brown oil. The oil was chromatographed on 150 g silica gel (sequentially eluted with chloroform, then 100:1 and 100:2 CHCl$_3$:MeOH/NH$_3$) to give 5.3 g (69% yield) of tetraethyl [2-methyl-3-(5-methyl-2-pyridinyl)-5-isoxazolidenylidene] bisphosphonate as a pale brown oil.

$^1$H NMR (CDCl$_3$, 200 MHz) δ 1.38 (m, 12H, CH$_2$CH$_3$), 2.33 (s, 3H, pyr-CH$_3$), 2.69 (s, 3H, NCH$_3$), 3.10 (m, 2H, CHCH$_2$), 4.00 (t, J=7 Hz, 1H, CHCH$_2$), 4.33 (m, 8H, CH$_2$CH$_3$), 7.47 (m, 2H, pyr-H), 8.26 (s, 1H, pyr-H).

Follow the procedure as described in Example 2 using TMSBr. Reaction time: 72 hours. Trituration with ethanol gave 2.0 g (50% yield) of [2-methyl-3-(5-methyl-2-pyridinyl)-5-isoxazolidenylidene] bisphosphonic acid as a white powder, m.p. 125° C. (dec.).

IR (KBr) 3400 (m), 2800 (m, broad), 1615 (m), 1555 (m), 1452 (m), 980 (s, broad), 915 (s, broad), 835 (m) cm$^{-1}$. MS (negative FAB) m/e (rel. intensity) 337 (M−H+, 100). $^1$H NMR (D$_2$O, 400 MHz) δ 2.49 (s, 3H, pyr-CH$_3$), 2.71 (s, 3H, NCH$_3$), 2.90 (m, 1H, CHCHH), 3.31 (m, 1H, CHCHH), 4.39 (broad, 1H, CHCH$_2$), 7.91 (d, J=8 Hz, 1H, pyr-H), 8.33 (d, J=8 Hz, 1H, pyr-H), 8.55 (s, 1H, pyr-H). $^{13}$C NMR (D$_2$O, 100 MHz) δ 17.1, 42.4, 43.0, 68.3, 80.9 (t, J=143 Hz), 126.3, 138.2, 141.5, 147.3, 148.4.

EXAMPLE 7

[2-Methyl-3-(6-methyl-2-pyridinyl)-5-isoxazolidenylidene]bisphosphonic acid

A mixture of ethenylidenebisphosphonate (20.0 g, 66.7 mmol) and N-[(6-methyl-2-pyridinyl)methylene]methanamine N-oxide (5.0 g, 33.3 mmol) was heated at 60° C. overnight. The resulting oil was subjected to an aqueous workup as described in Example 6 to give 13.3 g (89% yield) of pale brown oil. The oil was chromatographed on 600 g silica gel (sequentially eluted with 100:1 and 100:2 CHCl$_3$:MeOH/NH$_3$) to give 8.7 g (56% yield) of tetraethyl [2-methyl-3-(6-methyl-2-pyridinyl)-5-isoxazolidenylidene] bisphosphonate as an oil.

$^1$H NMR (CDCl$_3$, 200 MHz) δ 1.39 (m, 12H, CH$_2$CH$_3$), 2.53 (s, 3H, pyr-CH$_3$), 2.70 (s, 3H, NCH$_3$), 3.12 (m, 2H, CHCH$_2$), 3.98 (dd, J=7 Hz, 11 Hz, 1H, CHCH$_2$), 4.31 (m, 8H, CH$_2$CH$_3$), 7.06 (d, J=8 Hz, 1H, pyr-H), 7.37 (d, J=8 Hz, 1H, pyr-H), 7.57 (t, J=8 Hz, 1H, pyr-H).

Follow the procedure as described in Example 2 using TMSBr. Reaction time: 68 hours. Trituration with methanol gave 4.8 g (75% yield) of [2-methyl-3-(6-methyl-2-pyridinyl)-5-isoxazolidenylidene] bisphosphonic acid as a white powder, m.p. 180° C. (dec.).

IR (KBr) 2660 (m,broad), 1645 (s), 1613 (s), 1448 (m), 975 (s), 912 (s) cm$^{-1}$. MS (negative FAB) m/e (rel. intensity) 337 (M−H$^+$, 100). $^1$H NMR (D$_2$O, 400 MHz) δ 2.68 (s, 3H, pyr-C$\underline{H}_3$), 2.74 (s, 3H, NC$\underline{H}_3$), 2.90 (m, 1H, CHC$\underline{H}$H), 3.30 (m, 1H, CHCH$\underline{H}$), 4.28 (broad t, J=7 Hz, 1H, C$\underline{H}$CH$_2$), 7.75 (d, J=8 Hz, 1H, pyr-$\underline{H}$), 7.81 (d, J=8 Hz, 1H, pyr-$\underline{H}$), 8.33 (t, J=8 Hz, 1H, pyr-$\underline{H}$).

EXAMPLE 8

[2-Ethyl-3-(2-pyridinyl)-5-isoxazolidenylidene]bisphosphonic acid

A mixture of ethenylidenebisphosphonate (12.0 g, 40.0 mmol) and N-(2-pyridinylmethylene)ethanamine N-oxide (3.00 g, 20.0 mmol) was heated at 68° C. for 4 days. The resulting oil was chromatographed on 1 Kg silica gel (100:1 CHCl$_3$:MeOH/NH$_3$) to give 6.1 g (68% yield) of tetraethyl [2-ethyl-3-(2-pyridinyl)-5-isoxazolidenylidene] bisphosphonate as a viscous brown oil.

$^1$H NMR (CDCl$_3$, 200 MHz) δ 1.12 (t, J=7.5 Hz, 3H, NCH$_2$C$\underline{H}_3$), 1.37 (m, 12H, CH$_2$C$\underline{H}_3$), 2.85 (q, J=7.5 Hz, 2H, NC$\underline{H}_2$CH$_3$), 3.12 (m, 2H, C$\underline{H}$CH$_2$), 4.15 and 4.31 (overlapping m, 9H, NCHC$\underline{H}_2$ and C$\underline{H}_2$CH$_3$), 7.22 (dd, J=5 Hz, 8 Hz, 1H, pyr-$\underline{H}$), 7.61 (d, J=8 Hz, 1H, pyr-$\underline{H}$), 7.68 (d, J=8 Hz, 1H, pyr-$\underline{H}$), 8.52 (d, J=5 Hz, 1H, pyr-$\underline{H}$).

Follow the procedure as described in Example 2 using TMSBr. Reaction time: 3 days. Trituration with ethanol, followed by recrystallization from water-ethanol gave 1.57 g (34% yield) of [2-ethyl-3-(2-pyridinyl)-5-isoxazolidenylidene] bisphosphonic acid as a green powder, m.p. 124° C. (swelling).

IR (KBr) 3405 (m, broad), 1619 (m), 1110 (m, broad) cm$^{-1}$. MS (negative FAB) m/e (rel. intensity) 337 (M−H, 100). $^1$H NMR (DCl/D$_2$O, 400 MHz) δ 1.00 (t, J=7 Hz, 3H, CH$_2$C$\underline{H}_3$), 2.88 (overlapping m, 2H, C$\underline{H}$HCH$_3$ and CHC$\underline{H}$H), 3.06 (m, 1H, CH$\underline{H}$CH$_3$), 3.34 (m, 1H, CHCH$\underline{H}$), 4.66 (t, 1H, C$\underline{H}$CH$_2$), 7.88 (m, 1H, pyr-$\underline{H}$), 7.98 (d, J=8 Hz, 1H, pyr-$\underline{H}$), 8.43 (t, J=8 Hz, 1H, pyr-$\underline{H}$), 8.60 (d, J=6 Hz, 1H, pyr-$\underline{H}$).

EXAMPLE 9

[2-(Phenylmethyl)-4-isoxazolidenylidene]bisphosphonic acid

A solution of tetraethyl [2-(phenylmethyl)-5-isoxazolidenylidene] bisphosphonate (4.46 g, 10.3 mmol) in dioxane (100 mL) under nitrogen was heated at 70° C. for 48 hours. The solution was cooled to 25° C. and concentrated in vacuo to give 4.22 g (95% yield) of oil. The oil was chromatographed on ca. 250 g silica gel (100:3 ethyl acetate:Et$_3$N) to give 3.49 g (78% yield) of tetraethyl [2-(phenylmethyl)-4-isoxazolidenylidene] bisphosphonate as a pale yellow oil.

MS (FAB) m/e (rel. intensity) 436 (M+H, 65), 91 (PhCH$_2^+$, 100). MS (negative FAB) 406 (M−Et, 100). $^1$H NMR (CDCl$_3$, 200 MHz) δ 1.34 (m, 12H, CH$_2$C$\underline{H}_3$), 2.80−3.75 (broad m, 2H, NCH$_2$), 3.75−4.45 (broad overlapping s and m, 12H, NC$\underline{H}_2$Ph, C$\underline{H}_2$CH$_3$, OC$\underline{H}_2$), 7.30 (m, 3H, Ar$\underline{H}$), 7.37 (d, J=7 Hz, 2H, Ar$\underline{H}$). $^{13}$C NMR (CDCl$_3$, 100 MHz) δ 16.3, 51.6 (t, J=138 Hz), 57.9, 61.2, 63.2, 68.9, 127.4, 128.3, 128.9, 136.5.

Follow the procedure as described in Example 2 using TMSBr. Reaction time: 72 hours. Trituration with ethanol gave 1.90 g (80% yield) of [2-(phenylmethyl)-4-isoxazolidenylidene] bisphosphonic acid as a white powder, m.p. 165° C. (dec.).

IR (KBr) 2500 (m, broad), 1615 (m), 1450 (m), 1123 (m), 988 (s), 740 (m) cm$^{-1}$. MS (FAB) m/e (rel. intesity), 324 (M+H$^+$, 32), 91(PhCH$_2^+$100). $^1$H NMR (DMSO, 200 MHz) δ 2.90−3.70 (broad, 2H, NC$\underline{H}_2$), 3.80−4.30 and 4.00 (overlapping m and s, 4H, OC$\underline{H}_2$ and NC$\underline{H}_2$ Ar), 7.32 (m, 5H, Ar$\underline{H}$), 9.88 (broad s, 4H, PO$_3$$\underline{H}_2$). $^{13}$C NMR (DMSO, 100 MHz) δ 51.0 (t, J=127 Hz), 57.8, 60.4, 68.7, 127.3, 128.2, 129.1, 137.0.

Elemental analysis for C$_{10}$H$_{15}$NO$_7$P$_2$.0.27 H$_2$O: Calc'd: C, 36.61; H, 4.77; N, 4.27. Found: C, 36.43; H, 4.93; N, 3.99.

EXAMPLE 10

[2-Methyl-3-(2-pyridinyl)-5-isoxazolidenylidene]bisphosphonic acid sodium salt

To a solution of [2-Methyl-3-(2-pyridinyl)-5-isoxazolidenylidene]bisphosphonic acid (4.29 mmol) in water (10 mL) was added sodium bicarbonate (4.29 mmol) portion-wise as a solid. Concentration in vacuo gave a hard foam which was triturated with methanol (20 mL). Isolation of the solid by centrifugation gave the sodium salt as a hemihydrate. After drying in vacuo, a gray powder (1.26 g) was obtained, m.p. 174° C.

Elemental analysis for C$_9$H$_{13}$N$_2$O$_7$P$_2$Na.½H$_2$O: Calc'd: C, 30.44; H, 3.97; N, 7.89. Found: C, 30.12; H, 4.01; N, 7.61.

What is claimed is:

1. A compound of the formula:

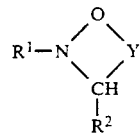

in which

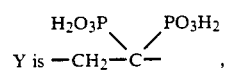

positioned so that the gem-diphosphonic acid carbon atom is in the 4- or 5- position;

R$^1$ is alkyl of 1 to 6 carbon atoms or arylalkyl of 7 to 12 carbon atoms;

R$^2$ is hydrogen, 2- or 3-pyridinyl or 3-,5- or 6-alkylpyridin-2-yl in which the alkyl substituent has 1 to 6 carbon atoms;

or a pharmaceutically acceptable salt thereof, with the proviso that when the gem-bisphosphonic acid substituted carbon atom is in 4-position, R$^1$ is other than alkyl.

2. A compound of claim 1 in which the free phosphonic acids are in 5-position, R$^1$ is methyl and R$^2$ is hydrogen, 2- or 3-pyridinyl or 3-or 5-methylpyridin-2-yl, or a pharmaceutically acceptable salt thereof.

3. A compound of claim 1 in which the free phosphonic acid groups are in 5-position, R$^1$ is methyl and R$^2$ is 2-pyridinyl or 3-methylpyridin-2-yl, or a pharmaceutically acceptable salt thereof.

4. A compound of claim 1 which is (2-methyl-5-isoxazolidenylidene)bisphosphonic acid, or a pharmaceutically acceptable salt thereof.

5. A compound of claim 1 which is [2-(phenylmethyl)-5-isoxazolidenylidene]bisphosphonic acid, or a pharmaceutically acceptable salt thereof.

6. A compound of claim 1 which is [2-methyl-3-(2-pyridinyl)-5-isoxazolidenylidene]bisphosphonic acid, or a pharmaceutically acceptable salt thereof.

7. A compound of claim 1 which is [2-methyl-3-(3-pyridinyl)-5-isoxazolidenylidene]bisphosphonic acid, or a pharmaceutically acceptable salt thereof.

8. A compound of claim 1 which is [2-methyl-3-(3methyl-(2-pyridinyl)-5-isoxazolidenylidene]bisphosphonic acid, or a pharmaceutically acceptable salt thereof.

9. A compound of claim 1 which is [2-methyl-3-(5-methyl-2-pyridinyl)-5-isoxazolidenylidene]bisphosphonic acid, or a pharmaceutically acceptalbe salt thereof.

10. A compound of claim 1 which is [2-methyl-3-(6-methyl-2-pyridinyl)-5-isoxazolidenylidene]bisphosphonic acid, or a pharmaceutically acceptable salt thereof.

11. A compound of claim 1 which is [2-ethyl-3-(2-pyridinyl)-5-isoxazolidenylidene]bisphosphonic acid, or a pharmaceutically acceptable salt thereof.

12. A compound of claim 1 which is [2-(phenylmethyl)-4-isoxazolidenylidene]bisphosphonic acid, or a pharmaceutically acceptable salt thereof.

13. A compound of claim 1 which is [2-methyl-3-(2-pyridinyl)-5-isoxazolidenylidene]bisphosphonic acid sodium salt, or a pharmaceutically acceptable salt thereof.

14. A method for the treatment of osteoporosis which comprises administering to a patient in need of such treatment, as an active ingredient, an effective amount of a compound of the formula:

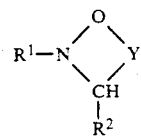

in which

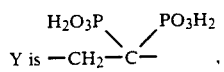

positioned so that the gem-diphosphonic acid carbon atom is in the 4- or 5- position;

$R^1$ is alkyl of 1 to 6 carbon atoms or arylalkyl of 7 to 12 carbon atoms;

$R^2$ is hydrogen, 2- or 3-pyridinyl or 3-,5- or 6-alkyl-pyridin-2-yl in which the alkyl substituent has 1 to 6 carbon atoms;

or a pharmaceutically acceptable salt thereof, with the proviso that when the gem-bisphosphonic acid substituted carbon atom is in 4-position, $R^1$ is other than alkyl.

15. A method of claim 14 in which said compound is [2-methyl-3-(2-pyridinyl)-5-isoxazolidenylidene]bisphosphonic acid, or a pharmaceutically acceptable salt thereof.

16. A method of claim 14 in which said compound is [2-methyl-3-(3-methyl-2-pyridinyl)-5-isoxazolidenylidene]bisphosphonic acid, or a pharmaceutically acceptable salt thereof.

* * * * *